United States Patent [19]

Taylor

[11] Patent Number: 5,725,777
[45] Date of Patent: *Mar. 10, 1998

[54] REAGENT/DRUG CARTRIDGE

[75] Inventor: Michael A. Taylor, Encinitas, Calif.

[73] Assignee: PrisMedical Corporation, Napa, Calif.

[*] Notice: The term of this patent shall not extend beyond the expiration date of Pat. No. 5,259,954.

[21] Appl. No.: 149,319

[22] Filed: Nov. 9, 1993

Related U.S. Application Data

[63] Continuation-in-part of Ser. No. 809,272, Dec. 16, 1991, Pat. No. 5,259,954.

[51] Int. Cl.$^6$ .................................... B01D 61/00
[52] U.S. Cl. ................... 210/650; 210/232; 210/257.1; 210/259; 604/416; 604/221
[58] Field of Search .................... 210/352, 259, 210/651, 232, 257.1, 257.2, 660, 350; 604/416, 111, 410, 56, 221; 422/101

[56] References Cited

U.S. PATENT DOCUMENTS

| | | |
|---|---|---|
| 3,276,458 | 10/1966 | Iversen et al. . |
| 3,517,816 | 6/1970 | Huppen ............................ 210/352 X |
| 4,070,289 | 1/1978 | Akcasu . |
| 4,160,727 | 7/1979 | Harris, Jr. . |
| 4,280,912 | 7/1981 | Berry, III et al. . |
| 4,396,383 | 8/1983 | Hart . |
| 4,458,733 | 7/1984 | Lyons ............................... 604/410 |
| 4,484,920 | 11/1984 | Kaufman ............................ 604/416 |
| 4,507,114 | 3/1985 | Bohman et al. .................... 604/411 |
| 4,576,603 | 3/1986 | Moss . |
| 4,648,978 | 3/1987 | Makinen et al. . |
| 4,698,153 | 10/1987 | Matsuzaki et al. . |
| 4,784,763 | 11/1988 | Hambleton et al. . |
| 4,810,388 | 3/1989 | Trasen . |
| 4,871,463 | 10/1989 | Taylor et al. ....................... 210/161 |
| 4,994,056 | 2/1991 | Ikeda . |
| 5,004,535 | 4/1991 | Bosko et al. . |
| 5,032,265 | 7/1991 | Jha et al. . |
| 5,059,317 | 10/1991 | Marius et al. . |
| 5,259,954 | 11/1993 | Taylor ............................... 210/232 |

FOREIGN PATENT DOCUMENTS 2346239   2/1977   France .

*Primary Examiner*—Ana Fortuna

[57] ABSTRACT

A reagent cartridge for reacting a soluble reagent with a fluid diluent is disclosed having a fluid inlet for accepting a diluent and fluid outlet for expelling a solution. The cartridge casing also has fluid manifolds adjacent to the inlet and the outlet for directing fluid in a radial direction from the inlet to the outlet. The casing further defines a receptacle for a soluble reagent. A volumetric compensation means for volumetrically compensating for dissolution of the reagent upon introduction of the diluent into the fluid inlet is provided. The volumetric compensation means can take the form of a resilient sponge material having a compressed volume and an expanded volume, wherein the expanded volume is up to at least 500% of the compressed volume. The volumetric compensation means can also take the form of resilient coil springs. In other embodiments, a fluid permeable pressure plate is positioned adjacent to a free end of the coil spring and the reagent is positioned against the pressure plate. A method for obtaining injectable quality intravenous solutions in the field using the reagent cartridge is also disclosed.

8 Claims, 7 Drawing Sheets

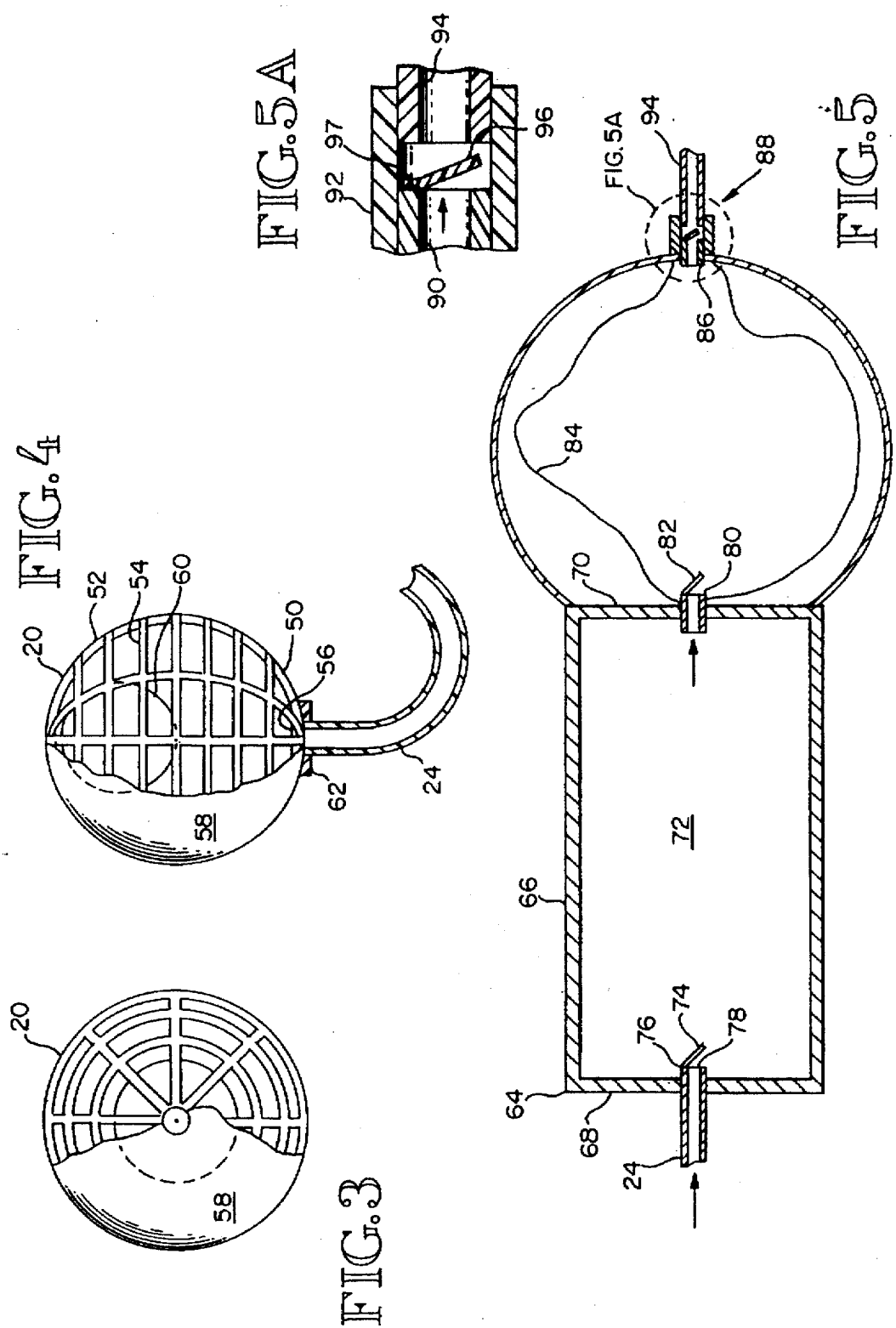

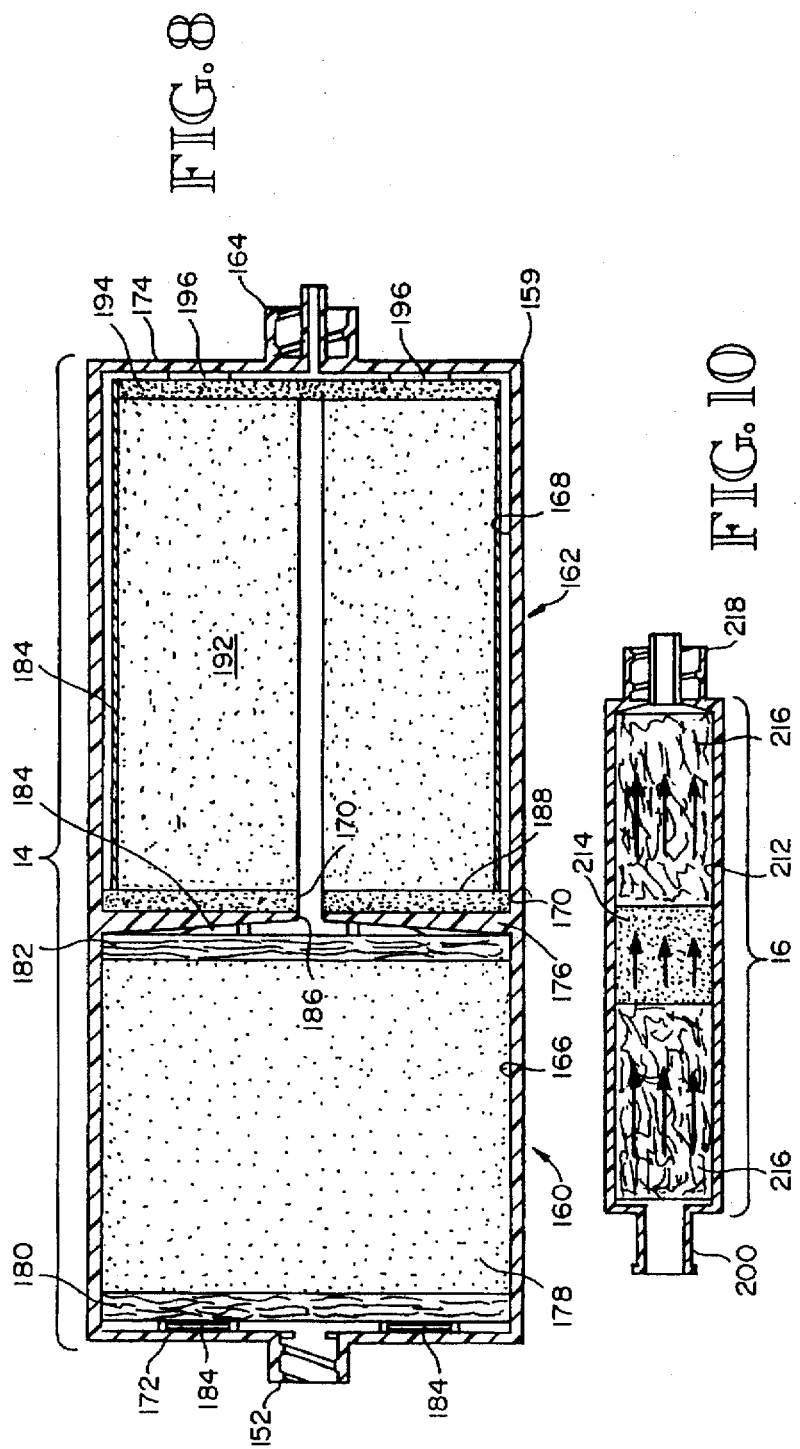

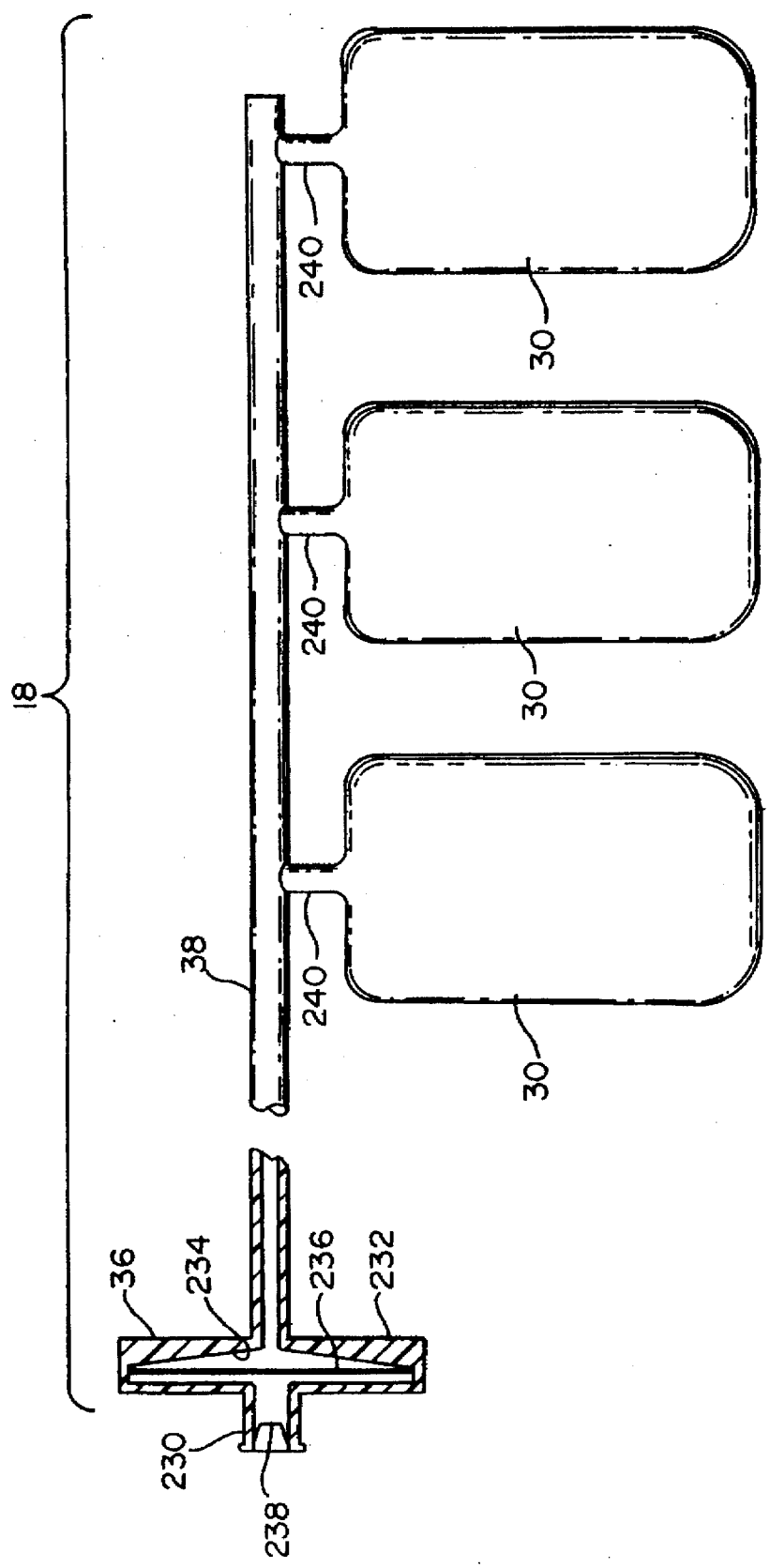

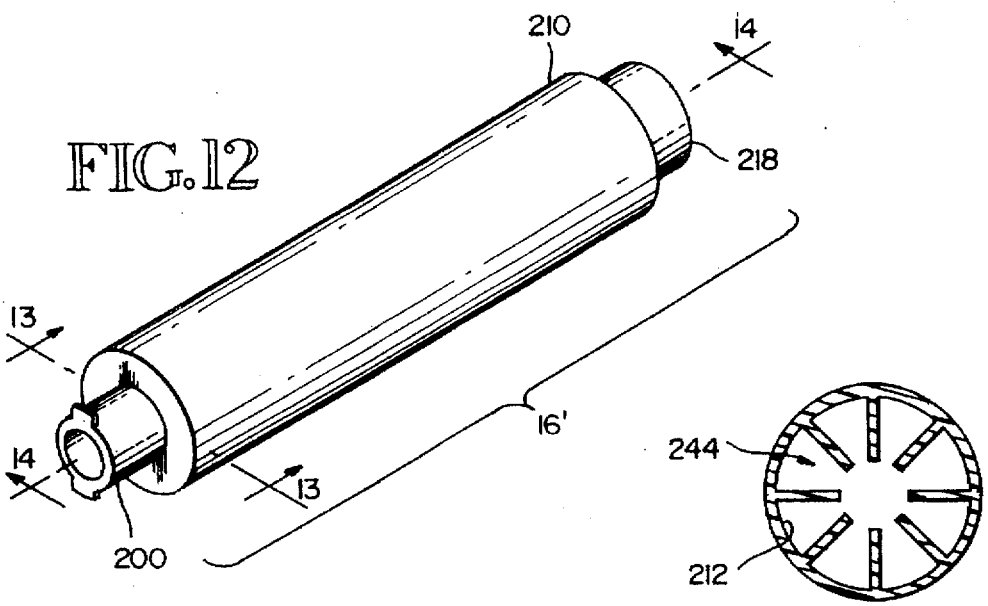
FIG. 12
FIG. 13
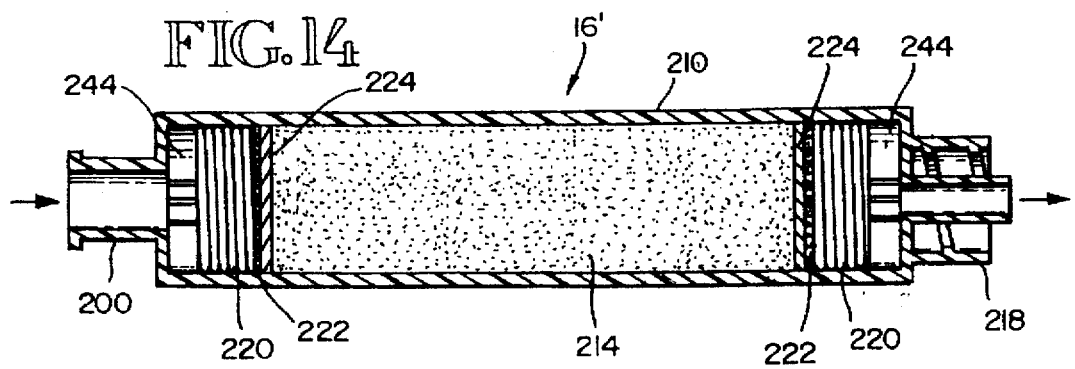
FIG. 14
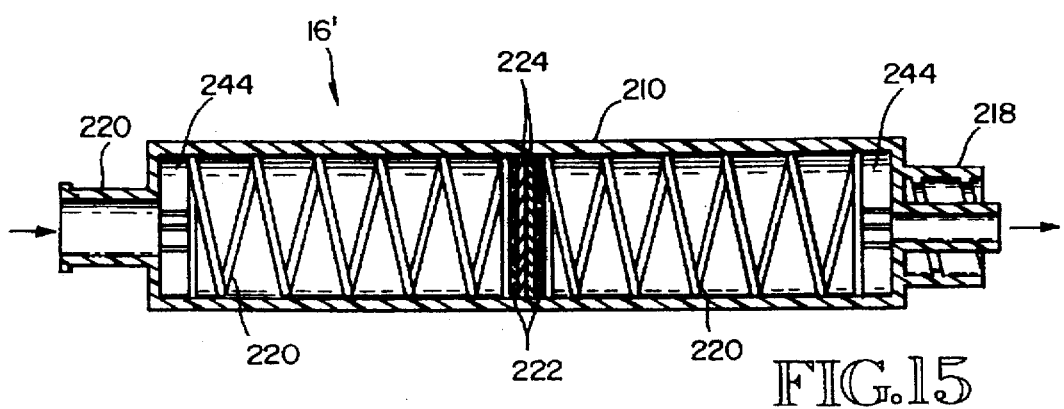
FIG. 15

& 1

REAGENT/DRUG CARTRIDGE

CROSS-REFERENCE TO RELATED APPLICATION

This application is a continuation-in-part of U.S. application Ser. No. 07/809,272 filed Dec. 16, 1991, now U.S. Pat. No. 5,259,954.

TECHNICAL FIELD

The invention relates to methods and apparatus for purifying water, and methods and apparatus for preparation of intravenous solutions. More specifically, the invention relates to methods and apparatus for preparing intravenous solutions in the field.

BACKGROUND OF THE ART

Severe trauma to the human body often involves significant loss of body fluids. In addition, a variety of illnesses, whether microbial or vital cause severe diarrhea followed by dehydration and ion imbalance. In the absence of rapid rehydration an individual will quickly die.

The most rapid, and sometimes the only practical method for rehydrating an individual is injection of an intravenous saline or dextrose solution. Such treatment is quite common and readily obtained in metropolitan areas where apparatus for purifying water to intravenously injectable quality, and for storing prepared intravenous solutions are readily available. However, in many areas of the world such facilities are not available and the problem of providing substantial quantities of intravenous solutions on short notice has not been adequately resolved. In addition, various activities which tend to occur in remote areas, such as military operations or space exploration expose individuals to the possibility of traumatic injury or the sudden onset of dehydrating illnesses where prepared, sterilized water, intravenous solutions, or solution preparation equipment are not available.

There are two particular problems which are associated with providing intravenous solutions in the field. The first problem involves the production of injectable quality water for the preparation of an intravenous solution. The second involves the storage of such solutions.

In U.S. Pat. No. 4,610,684 to Knox et al. these problems are addresses by providing a flexible intravenous fluid bag having two separate compartments. In a first compartment, self sealing ports are provided for the introduction of sterile water. A powdered reagent is stored in the second compartment. After sterile water is introduced into the first chamber, a seal between the two chambers is ruptured so that the sterile water can mix with the reagent. The Knox apparatus avoids some of the problems associated with crystal formations or clumping of reagents, and evaporation of the liquid component of the resulting solution through the vinyl sidewalls of the intravenous pack because the sterile water is introduced into the bag at the time of use. However, a source of injectable quality water must be available at the point of use, and in military operations, third world countries, etc. such sterile water sources are often unavailable. U.S. Pat. No. 4,484,920 to Kaufman et al., and U.S. Pat. No. 4,994,056 to Ikeda also disclose multi-compartment intravenous bags for mixing sterile water with a powdered reagent.

The present state of the art for producing potable or injectable quality water is well developed. A typical apparatus describing the purification steps to produce ultra pure water for research in commercial applications is disclosed in U.S. Pat. No. 4,280,912 to Berry, III et al. The standards for potable water are set forth in 40 CFR §§141.11 et seq. However, potable quality water is not sufficiently pure for injection into the human body. In addition to removal of the toxins, as set forth in 40 CFR §141.11 et sec, infectious biological agents such as microscopic plants, bacteria, viruses and pyrogens having particle sizes as small as 0.002 µm must be removed. Particle size as small as 0.002 µm is approximately at the maximum effectiveness of ultra filtration techniques.

Portable microfiltration apparatus are available for campers which are capable of filtering out most bacteria to a particle size of approximately 0.2 µm. Water at this purity level is potable but is not suitable for injection to the human body. Therefore, there is no portable ultra filtration device which can produce injectable quality water for use with the above described compartmentalized intravenous mixing bags. As a result, there is no effective way to prepare intravenous solutions in the field in the absence of an injectable quality water source.

Therefore, a need exists for a method and apparatus which allow the preparation of various intravenous solutions in the field without access to sources of ultra pure, injectable quality water, or storage facilities for premixed intravenous solutions.

SUMMARY OF THE INVENTION

It is therefore an object of the present invention to provide a method and apparatus for preparing intravenous solutions in the field from sources of impure, raw water.

The invention achieves this object, and other objects and advantages which will become apparent from the description which follows by providing a portable, modular intravenous solution preparation apparatus. The apparatus includes a first module which microfilters and detoxifies raw water from a raw water intake. A second module deionizes the treated water and removes any remaining biological contaminants from the deionized, detoxified water. A third module contains a predetermined quantity of reagent to produce the desired intravenous solution which can then be collected in an appropriate receptacle.

In its preferred embodiment, all of the modules are sterile and a fourth module having a sterilization-filtration capability can be inserted intermediate the consumable reagent module and the receptacle for the intravenous solution. Fluid permeable volumetric expansion mechanisms are provided in the third module to compensate for volumetric contraction of the reagent because the reagent in the third module can be a soluble material. Such volumetric compensation is necessary to prevent the formation of voids and channels in the reagent which would otherwise effect the resulting concentration of the intravenous solution. In addition, other volume compensating mechanisms are provided in the second module to compensate for volumetric changes in an ion exchange stage and in an activated carbon stage.

A pressure compensating mechanism is provided in the first module to maintain hydraulic pressure in a reverse osmosis stage within a desired range.

The first module also has a substantially buoyant, raw water intake mechanism. The mechanism positions a fluid intake port at a preferred distance below the surface of a water body to avoid clogging with plants and biologicals concentrated at the water surface and to avoid collection of dissolved contaminants which tend to concentrate in the sedimentary layers at the bottom of the body of water. Consequently, the mechanism also positions the fluid intake port away from the bottom where agricultural contaminants such as pesticides and fertilizers, plant and bacterial matter tend to concentrate.

A final ultra filtration mechanism of a fourth module can be positioned between the output of the reagent module and the appropriate intravenous solution receptacle to ensure the sterility of the intravenous solution. Furthermore, multiple intravenous solution bags can be connected to the fluid distribution manifold for preparation of solutions having a low reagent concentration. An individual bag can be isolated by the use of hemostats applied to the manifold branches. Once the selected intravenous bag has been filled, the bag can be separated from the manifold by the application of heated forceps.

In a preferred embodiment, a first, second, third and fourth module are interconnected by fluid connection mechanisms which mate only with the appropriate connection mechanism on the appropriate module. Thus, the modules cannot be arranged in an improper sequence.

BRIEF DESCRIPTION OF THE DRAWINGS

FIG. 3 is a top plan view of the raw water intake mechanism of the invention with a portion cut away.

FIG. 4 is a side elevational view of the intake mechanism of FIG. 3.

FIG. 5 is a sectional, side elevational view of a pressure generating and pressure regulating stage of the first module of the invention illustrating blockage resistant one-way fluid valves.

FIG. 5a is an enlarged, sectional, side elevational view of circled area 5a of FIG. 5.

FIG. 8 is a sectional, side elevational view of a second module of the invention employing an ion exchange chamber and an activated carbon chamber.

FIG. 9 is a sectional, side elevational view of a consumable reagent module prior to use.

FIG. 10 is a sectional, side elevational view of the reagent module shown in FIG. 9 after use.

FIG. 11 is a sectional, side elevational view of the fourth module of the invention illustrating a fluid distribution manifold for multiple intravenous solution bags.

FIG. 12 is an enlarged, isometric view of a consumable reagent module shown in FIGS. 9 and 10.

FIG. 13 is a cross sectional view taken along line 13—13 of FIG. 12.

FIG. 14 is a cross sectional view taken along line 14—14 of FIG. 12 of an alternate embodiment of the reagent module before the reagent has been consumed.

FIG. 15 is a sectional, elevational view similar to FIG. 14 after the reagent has been consumed.

BEST MODE FOR CARRYING OUT THE INVENTION

Figure 1:
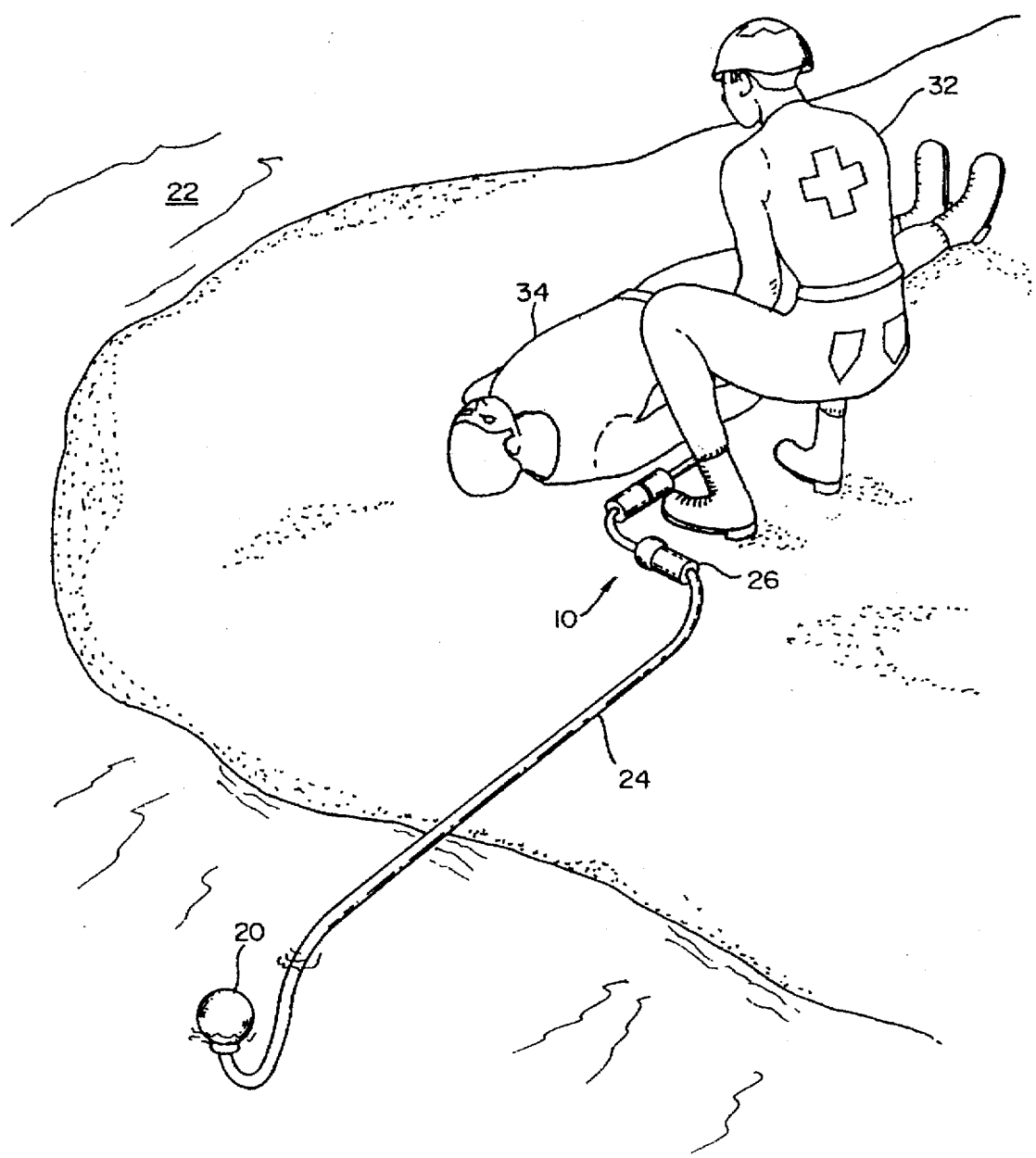
FIG. 1 is an environmental view of the portable intravenous solution preparation apparatus and method in use on a traumatized individual.
Figure 2:
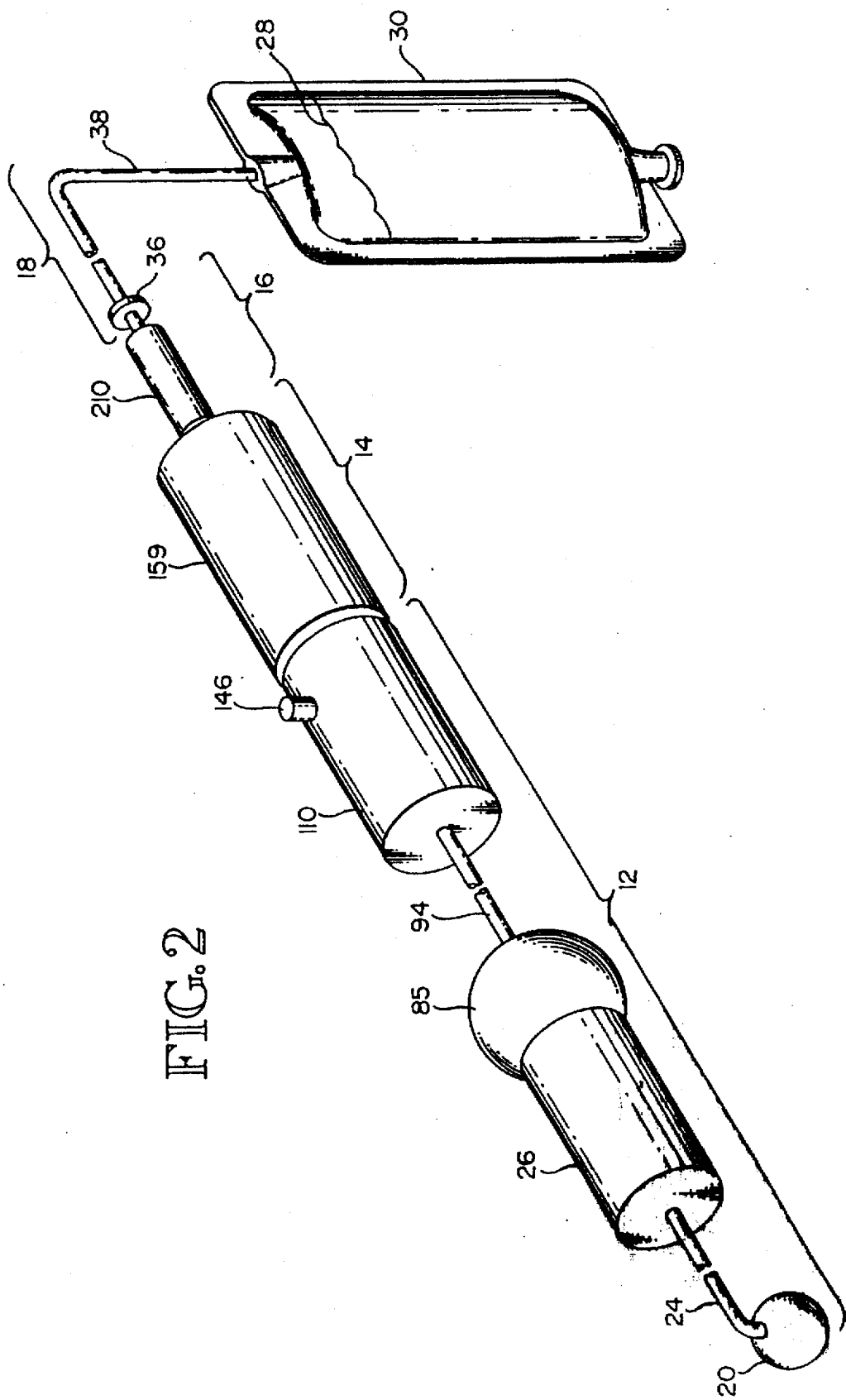
FIG. 2 is an isometric view of the first, second, third and fourth modules of the invention.
Figure 6:
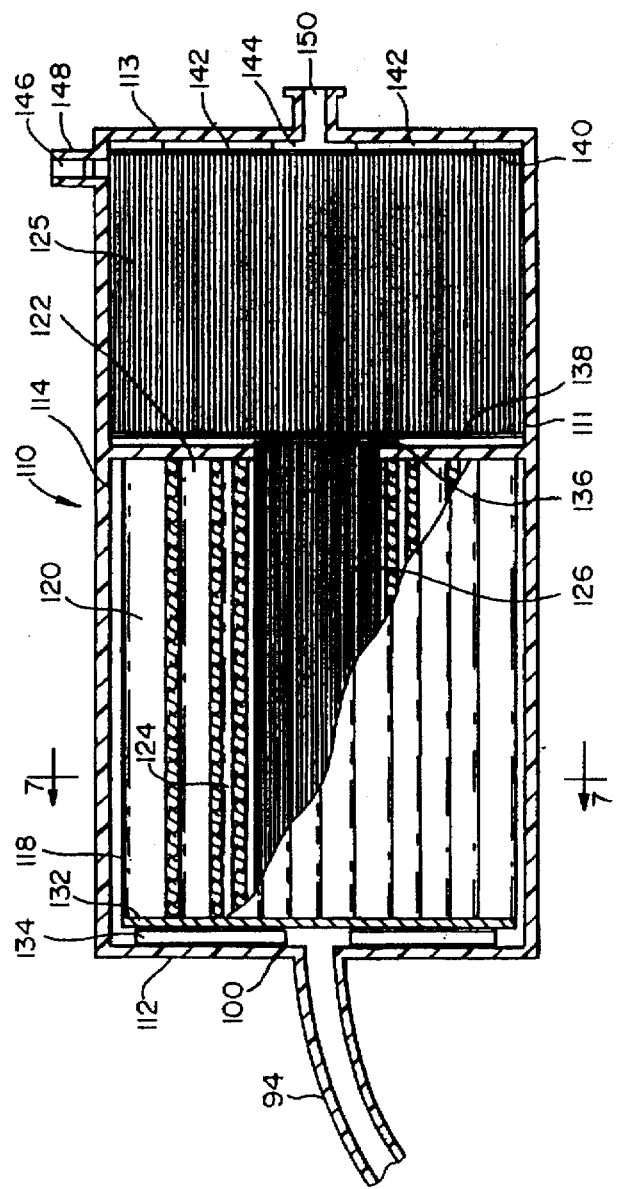
FIG. 6 is a sectional, side elevational view of a microfiltration/reverse osmosis stage of the first module of the invention.

A portable intravenous solution preparation apparatus, in accordance with the principles of the invention is generally indicated at reference numeral 10 in FIGS. 1 and 2. As best shown in FIG. 2, the apparatus is preferably modular and includes a potable water maker module 12, an injectable water maker module 14, a reagent module 16, and a sterilization and storage module 18.

The potable water maker module 12 has a raw water strainer 20 which, as best seen in FIG. 1 is substantially buoyant and which serves as an intake for drawing raw water, such as from a pond 22 through an elongated, flexible intake hose 24 and into a pump stage 26 for further processing by the apparatus. The apparatus ultimately produces an intravenously injectable solution (IV solution) 28 in an intravenous solution bag (IV bag) 30 which may be administered by a qualified medical technician 32 to a patient 34.

The potable water maker module 12 is reusable and has the capacity to process approximately 1,000 liters of raw water before replacement is necessary. The raw water which is processed by the potable water maker module 12 has sufficient purity for drinking, but is not sufficiently pure for intravenous injection. The injectable water maker module 14 further processes the potable water emanating from the potable water maker module 12 and produces water sufficient in quality for intravenous injection into the human body and for additional processing in the reagent module 16. The reagent module reacts with the injectable quality water (diluent) from the injectable water maker module 14 with an appropriate reagent drug such as calcium chloride, sodium chloride, dextrose, lidocaine hydrochloride, dopamine hydrochloride, alcohol, or various combinations thereof to produce an intravenous solution of the proper concentration. The intravenous solution then passes through a final sterility filter 36 before entering the IV solution bag 30. The IV solution bag is connected to the sterility filter by a medical grade quarter-inch diameter polyvinyl chloride (PVC) outlet tube 38 which can be severed and cauterized by a pair of heated forceps to separate the IV bag 30 from the sterility filter 36. The IV bag 30 is then ready for use in the conventional manner.

As will be described further hereinbelow, each of the modules have respective fluid inlets and outlets which are mechanically connectable only to the appropriate inlet or outlet of the appropriate module. Thus, the system can be assembled in the field under exigent circumstances without the possibility of mismatching the modules or connecting the modules out of sequence. The system has been constructed in a modular fashion so that modules which have a relatively long life cycle (such as the potable water maker module 12 which has a life cycle of approximately 1,000 liters) will not have to be discarded when, for example, a reagent module 16 is exhausted (a reagent module typically will only produce one liter of solution) or if a component such as the injectable water maker module 14 malfunctions prematurely (this module should have a life cycle of more than 1,000 liters). The system 10 is therefore well adapted for use in the field because a minimum quantity of stock on hand need be maintained. In addition, by connecting various different reagent modules 16 in a preselected sequence, a variety of different intravenous solutions, with the correct concentrations can be prepared.

The raw water strainer 20 as best seen in FIGS. 3 and 4, has a spherical frame consisting of longitudinal ribs 52 and latitudinal ribs 54 and is preferably molded in halves from a rigid thermoplastic material. The frame 50 has a preferred diameter of approximately three inches. The frame 50 defines an inlet port 56 which is connected to the intake hose 24. The exterior frame 50 is covered with a macroporous covering 58 having a porosity of approximately 50 µm. A suitable covering can be obtained from Web Dynamics, Flanders, N.J., U.S.A. This fabric serves a gross filtering function for the potable water maker module 12.

The frame 50 contains a buoyancy sphere 60 manufactured from a fluid impermeable material such as polyethylene and has a diameter of approximately one-half inch. A metal washer 62 is bonded to the outside of the frame, adjacent the inlet port 56 and around the intake hose 24 so that when the raw water strainer is placed in a body of water, the intake port 56 will repose in an upright position approximately two inches below the surface of the water. This placement advantageously isolates the inlet port from undesirable macrophytes and phytoplankton, algae blooms, etc. which tend to reside at the water's surface. This placement also isolates the inlet port 56 from sedimentary materials at the bottom of a pond or shoreline. These materials include undesirable microbes, insoluble organics, insoluble pesticides, insoluble inorganics including heavy metals and aggregates or combinations of these contaminants.

The surface area of the strainer 20 is sufficiently large to allow raw water to pass through the macroporous covering passively and collect in a pool above the inlet port for subsequent processing through the potable water maker 12.

The intake hose 24 terminates in a cylindrical pump chamber 64. The pump chamber has a resilient sidewall 66 bonded to a circular inlet wall 68 and a circular outlet wall 70 so as to define an interior volume 72 of approximately twenty-two cubic inches. The walls are preferably manufactured from medical grade polyvinyl chloride (PVC) in a thickness of approximately one-quarter inch. The inlet and outlet walls are bonded to the sidewall by a conventional bonding agent, or ultrasonic welding. The intake hose 24 penetrates an aperture in the inlet wall 68 and is bonded thereto to provide a fluid-tight and pressure resistant seal. A peripheral edge of small flap 74 of PVC material is bonded to an edge 76 of the end 78 of the intake hose. The flap 74 functions as a one-way valve because the flap is relatively flexible. It has been found that a conventional ball valve, and other types of conventional one-way valves tend to clog and become inoperative due to particulate matter becoming lodged in the seats of such valves. The flap structure shown tends to be self-cleaning and generally does not clog when particles smaller than 50 microns (which have been eliminated by the covering 58 shown in FIGS. 3 and 4) are encountered. The outlet wall 70 also has an aperture which receives a small section of tubing 80 with a similar one-way valve flap structure 82. Upon deformation of the resilient sidewall 56 by squeezing the same in the medical technician's hand, air is expelled from the volume 72. Upon releasing the sidewall 66, the resilient nature of the material draws filtered water through the raw water strainer 20 and into the volume. Subsequent compression of the sidewall 66 closes the flap 74, opens the flap 82 and expels the contents of the volume into a pressure regulating elastic sphere 84. The elastic sphere 84 is surrounded by a substantially less elastic, semi-rigid rubber outer sphere 85 to limit elastic deformation and to prevent bursting of the elastic sphere 84. The elastic sphere 84 forms a pressure regulating function which will be described in further detail hereinbelow.

The elastic sphere 84 has a diameter of approximately four inches and is constructed of a latex material having a thickness of approximately one-eighth inch and a modulus of elasticity of 2000 at 750% elastic deformation This outer sphere 85 is constructed from rubber, has a thickness of one-quarter inch, and a modulus of elasticity of 100 at 100% elongation. This sphere has an outlet 86 which receives a one-way valve mechanism 88, shown in greater detail in FIG. 5a.

The mechanism 88 has a first tube portion 90 which is received by and bonded to the outlet 86 of the latex sphere 84, and outer sphere 85. A collar 92 having an inner diameter sized to closely receive the outer diameter of the first tube portion 90 surrounds and extends beyond the portion of the first tube which protrudes from the latex sphere. The collar is also bonded to the outer sphere 85. A second tube portion 94 is also received in and bonded to the inner wall of the collar so as to form a gap of approximately one-quarter inch with respect to the first tube portion. A flap 96 of tubing material has a peripheral edge thereof bonded to a peripheral end portion 97 of the first tube portion 90 so as to function similar to the one-way valve structure 82 and flap 74 within the pump chamber 64.

Figure 7:
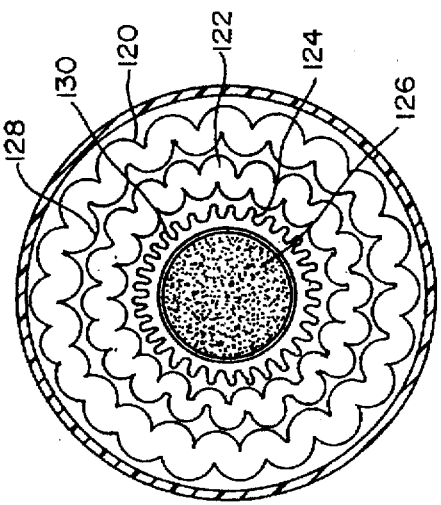
FIG. 7 is a sectional, top elevational view taken along lines 7—7 of FIG. 6.

The second tube portion 94 is connected to an inlet end 100 of a prefilter/reverse osmosis mechanism 110. The casing for the mechanism is preferably a medical grade of polypropylene having sufficient rigidity to withstand pressure in excess of 75 psi. A divider wall 111, and end caps 112, 113 define a cylindrical prefilter chamber 114 and a cylindrical reverse osmosis chamber 115. The prefilter chamber houses a multi-stage prefilter 118 consisting of first, second, third and fourth successively finer prefilters 120, 122, 124 and 126 respectively. As best seen in FIG. 7, the first, second and third prefilters are concentric with respect to one another and are separated by cylindrical, nylon mesh dividers 128, 130. The first, second and third prefilters are conventional, non-woven cellulose depth filters available from Cuono, Inc. Meriden, Conn. The first prefilter has a filtering capability of 100 µm, the second prefilter has a filtering capability of 30 µm, the third prefilter has a filtering capability of 1 µm, and the prefourth filter has a filtering capability of 0.1 µm. The ends of the prefilters adjacent to the inlet end 100 are embedded in or bonded to an end cap 132 made of the same material as the prefilter/reverse osmosis mechanism casing. This end cap is positioned in a spaced relationship from the inlet end cap 112 by radially directed fins 134 which permit fluid to flow radially from the second tube position 94 to the interior perimeter of the prefilter chamber 114. The first prefilter 120 is positioned in a radially spaced relationship with respect to the inside of the prefilter chamber so that all of the incoming fluid is exposed to the entire periphery of the first prefilter 120. The other ends of the first, second and third prefilters are embedded in, or bonded to the divider wall 111 so that fluid is forced to flow radially through the first, second and third prefilters. The end of the fourth prefilter distal from the inlet end 100 passes through the divider wall 111 at area 136.

The fourth prefilter comprises a bundle of ultrafiltration fibers available from Millipore, Malvern, Pa., U.S.A. Each fiber is essentially a hollow tube which is coated on the outside of the tube by a microfiltration membrane. Therefore, fluid flows radially into the tube and through the membrane (which performs the filtration function) and then axially through the center of the hollow tubes into the reverse osmosis chamber 115. The reverse osmosis chamber contains a reverse osmosis cartridge 137. The reverse osmosis cartridge consists of a plurality of hollow reverse osmosis fibers available from Hoerscht-Celeames, Philadelphia, Pa. Each fiber has its ends adjacent to the divider wall 111 sealed and embedded in a porous inlet plate 138 while the other ends of the reverse osmosis fibers are open and pass through a fluid impermeable support plate 140. The impermeable support plate 140 is supported in a spaced relationship from the outlet end cap 114 by radially directed fins 142. Thus, fluid flow through the reverse osmosis cartridge is axially directed through the porous inlet plate 138 and then radially into the reverse osmosis fibers, and then passes axially through the fibers and into a chamber 144 defined by support plate 140 and the outlet end cap 113. Concentrate flow including rejected ions and other waste materials exit through a concentrate water outlet 146 which penetrates the casing of the reverse osmosis chamber 115. A disk-shape flow restrictor 148 having a nominal aperture of approximately 0.01 inch is provided in the concentrate flow outlet port 146 to generate back pressure for the reverse osmosis cartridge. The flow restrictor is preferably manufactured of pliable material such as Viton® Rubber or silicon so that the cooperative effect of the flow restrictor 148, latex sphere 84, pump chamber 64 and one-way valve mechanism 88 establish a substantially continuous pressure of between 40 psi and 75 psi for effective operation of the reverse osmosis cartridge. As a result of the above activities, potable water is produced at an outlet end 150 of the potable water maker module 12.

The potable water maker outlet end 150 is configured as the male end of a conventional Luer lock. This outlet end only mates with an inlet end fitting 152 of the injectable water maker module 14 as best seen in FIG. 8. This module contains a deionizing stage generally indicated at reference numeral 160, and an activated carbon stage generally indicated at reference numeral 162 to produce water of injectable quality in an outlet end fitting 164. The deionizing stage 160 and activated carbon stage 162 are contained in a deionizing stage chamber 166 and an activated carbon stage chamber 168 respectively, and as defined by a cylindrical sidewall 170, inlet end cap 172, outlet end cap 174, and an internal, tapered divider wall 176.

The ion exchange stage has an ion exchange resin 178 such as quaternary aminoethyl Sephadex® (QAE-Sephadex)® or a diethyl aminoethyl Sephadex® (DEAE-Sephadex)® eletrolyte. These materials are substantially granular in nature and tend to expand or contract through osmotic action according to the pH of the fluid passing therethrough. To compensate for these volumetric changes and avoid the formation of channels of void in the ion exchange resin medium, the resin is contained between resilient frits 180, 182 which allow passage therethrough of fluid in an axial direction while expanding to compensate for decreases in the volume of the resin and contracting to compensate for expansion in the resin. The frits are supported by radially directed fins 184 in a spaced relation from the inlet end cap 172 and from the internal, tapered divider wall 176. The frits 180, 182 are preferably constructed from rolled and pressed cellulose depth filter; an appropriate item is grade 01AP cellulose manufactured by Cuono, Inc., Meriden, Conn. The structure of the deionizing stage 160 is substantially identical to the structure of the ion exchange column described in U.S. Pat. No. 4,871,463 entitled "Vertical Reaction Vessel" by Taylor et al., the disclosure of which is incorporated herein by reference.

The internal, tapered divider wall 176 has a centrally located aperture 186 which passes fluid therethrough which has been deionized in the deionizing stage 160. The activated carbon stage chamber 168 has an annular, fluid impermeable frit 188 located adjacent to the internal, tapered divider wall 176. The frit 188 also has a central, aperture 190 therein for the passage of fluid therethrough. The frit 188 supports an annular, activated carbon core 192 available from Calgon Carbon Corp., Pittsburgh, Pa., U.S.A. The core has a length of approximately three inches, an outer diameter of approximately 2.375 inches, and an interior diameter of approximately 0.125 inch. A fluid permeable, cylindrical support (not shown) lines the inner diameter of the annulus to prevent collapse of the core. Similarly, the outer diameter of the core is surrounded by a fluid permeable cylinder to prevent rupture of the core. The axial end of the core adjacent to the outlet end cap 174 is sealed by a circular frit 194 so that fluid flow is directed radially through the core. The frit 194 has a diameter which is slightly smaller than the diameter of the chamber 168, and is also maintained in a spaced relationship from the outlet end cap 174 by radially directed fins 196. The outer diameter of the core 192 is also slightly smaller than the inner diameter of the activated carbon stage chamber 168 so that after exiting the core radially, fluid flows axially down the inside wall of the chamber, past the frit 194 radially through the fins 196 and axially out of the outlet end fitting 164. The activated carbon core renders the water exiting the deionizing stage 160 suitable for intravenous injection. This water has all biogens, biological materials, toxic dissolved chemicals and other undesirable impurities sufficiently removed therefrom so as to constitute intravenously injectable water.

The outlet end fitting 164 is configured in a standard shape of a male Luer lock fitting. However, the fitting is substantially larger than a conventional Luer lock and mates only with the female inlet coupling 200 of the reagent cartridge module 16 as best seen in FIG. 9.

The reagent module 16 has an exterior casing 210 which defines an interior cavity 212 for a crystalline reagent 214 which is axially restrained by volumetrically compensating frits 216. The mechanical structure of this casing is substantially identical to the casing of U.S. Pat. No. 4,871,463 entitled "Vertical Reaction Vessel" by Taylor et al. which has been incorporated herein by reference. However, the frits 216 are substantially different from the frits 188, 194 of the activated carbon core, or the frits 180, 182 of the deionizing chamber 160. Frits 180, 182 of the deionizing chamber are preferably manufactured from cellulose as stated previously which can generally only expand to approximately 110% of their original volume. Such volumetric change is entirely adequate to compensate for expansion and contraction of the ion exchange resin. Similarly, the fluid impermeable frits 188, 194 of the activated carbon stage 162 are preferably manufactured from sponge rubber having a skin thereon formed by heat sealing. This material has the ability to compensate in volume to approximately plus or minus 10% of its original volume which is sufficient to compensate for the expected range of volume change in the length of the activated carbon core. However, the crystalline reagent 214 in the reagent module 216 is intended to be substantially consumed during the intravenous solution making process. Therefore, to avoid the formation of undesirable voids and channels in the reagent as the reagent dissolves, the frits must expand to compensate for the loss of volume. As shown in FIG. 10, once the reagent has been substantially exhausted, the frits may have to expand to over 500% of their original volume. Therefore, the preferred material for the frits 216 is a fluid permeable sponge rubber material. This material not only expands to compensate for dissolution of the reagent material, but also allows the fluid to pass therethrough but does, not allow the ion exchange reagent crystals themselves to pass therethrough. It is extremely important that voids and channels not form in the reagent during dissolution, otherwise the intravenous solution bag 30 will become filled with purified water which is not adequately reacted with the reagent resulting in the incorrect concentration of the solution.

The reagent module 16 also has an outlet 218 consisting of a fitting having a conventional, standard size male Luer lock configuration. The fitting has a standard size and is designed to mate only with a corresponding, standard size female Luer lock inlet coupling 230 on the sterilization filter 36 of the sterilization and storage module 18. The fitting pairs 200/164 and 152/150 which are upstream of the fitting pairs 218/230 are each 10% and 20% larger, respectively than a standard size Luer lock fitting to prevent coupling of the modules in the wrong order.

FIGS. 12 through 15 illustrate an alternate embodiment of the reagent module 16 designated as 16'. In this alternate embodiment, exterior casing 210 is identical to that used in the previous embodiment 16. That is, as shown in FIG. 13, this embodiment utilizes the same interior cavity 212, and fluid disbursal chambers 244 utilizing the radial fin arrangement described in my prior U.S. Pat. No. 4,871,463 which has been incorporated herein by reference. However, as best seen in FIG. 14, instead of using the volumetrically compensating frits 216 manufactured from a fluid permeable sponge rubber material, in place thereof are positioned coiled, stainless steel springs 220 having the ability as shown in FIG. 15 to expand to over 500% of their original volume to compensate for the dissolution of the reagent 214. The springs are preferably manufactured from a non-reactive material such as medical grade stainless steel and may be Teflon® coated. The coils have an inner diameter only slightly smaller than the inner diameter of the casing 210 so that the springs ride therein as pistons within a cylinder. One end of each coil rests on the fin structure 244 as shown in the figures. The other end of each spring supports a microporous support plate 222 which prevents the escape of reagent particles greater than approximately 1 μm. The support plate should be relatively rigid to prevent portions of the plate from coming into contact with one another prior to complete dissolution of the reagent 214. The expression of pressure on both sides of the reagent charge is therefore constant as the springs expand. The pressure is sufficient to compress the charge, minimizing the spaces between undissolved reagent particles. Uniformity of the expansion of the springs and the rigidity of the reagent microporous support plates contains the plates perpendicular to the longitudinal axis of the reagent. The porosity of the support plate can be varied to meet the requirements of different reagents. Thus, the porosity of the plate can be decreased by the use of porous membranes thereon, such as membranes 224 manufactured from non-woven polypropylene mesh to permit the pass of the fluid diluent therethrough, but retard the passage of the reagent crystals.

The sterilization filter 36 comprises a cylindrical housing 232 defining a conical interior compartment 234. The interior compartment houses a sterilization filter membrane 236 which is capable of filtering material larger then 0.02 μm. A filter of this type would become quickly clogged if the incoming solution has not been previously ultra filtered, deionized and treated in the previous stages.

One or more intravenous solution bags 30 may be connected to the outlet tube 38 as shown in the alternate embodiments of FIGS. 2 and 11. As previously stated, this tube whether in manifold form as shown in FIG. 11 or otherwise as shown in FIG. 2 can be severed from the sterility filter 36 by a pair of heated forceps. To maintain the sterility of the sterilization and storage module 18, a frangible, foil seal 238 is provided in the interior of the inlet coupling 230. Upon inserting the male end of the outlet 218 of the reagent module 16 into the female end of the coupling 230, the foil seal 238 will rupture permitting fluid to pass therethrough.

The multiple intravenous solution bag embodiment shown in FIG. 11 can be advantageously employed when a single patient or multiple patients need more than one type of intravenous solution. Multiple solutions can be prepared by merely changing the reagent cartridge (or coupling different reagent cartridges in sequence). In order to isolate a single reagent bag from the manifold, a hemostat can be placed on the manifold between the bag adjacent to the sterilizing filter and the next reagent bag. When the first reagent bag is full, that bag is removed by severing its neck 240 with a pair of heated forceps. This will "cauterize" the neck and maintain the sterility of the bag 30, the manifold 38, and any remaining bags. This procedure can then be repeated with the next bag in the sequence.

Various examples of reagent/intravenous solution preparations are listed below:

EXAMPLE I

Preparation of A One-Liter Intravenous Bag of Ringer's Solution

The reagent module 16 was loaded with 313 mg of calcium chloride, 300 mg of potassium chloride, and 8.6 grams of sodium chloride. The required volume for this quantity of reagent is 7.4 ml. The reagent module 16 has an inner diameter of 0.51 inch thus requiring a reagent column length of 2.25 inches which will result in a reagent with a volume of approximately 7.4 ml. The interior length of the reagent module is approximately 2.61 inches. Small fluid disbursement chambers 244 are provided at each end of the frits 216 adjacent to their respective inlet or outlets. The disbursement chambers have a height of approximately 0.03 inch providing an axial length of 0.15 inch for the frits 216. The above quantity of reagents assembled in the structure as recited will produce one liter of Ringer's solution for injection as long as voids and channels do not form in the reagent during dissolution.

EXAMPLE II

Preparation of a One-Liter Intravenous Bag of 5% Sodium Chloride Solution

The reagent module 16 was loaded with 50 g of Sodium Chloride. The required volume for this quantity of reagent is 40.0 ml. The reagent module 16 has an inner diameter of 0.75 inches thus requiring a reagent column length of 2.25 inches which will result in a reagent with a volume of approximately 40.0 ml. The interior length of the reagent module is approximately 2.61 inches. Small fluid disbursement chambers 244 are provided at each end of the frits 216 adjacent to their respective inlet or outlets. The disbursement chambers have a height of approximately 0.03 inch providing an axial length of 0.15 inch for the frits 216. The above quantity of reagents assembled in the structure as recited will produce one liter of Ringer's solution for injection as long as voids and channels do not form in the reagent during dissolution.

Those of ordinary skill in the art will perceive a variety of different reagent combinations which can be used to produce different solutions for intravenous injection utilizing the above apparatus and method. In addition, various modules of the system can be used alone or in different combinations. For example, the potable water maker module 12 includes a reusable potable water making module, an injectable water making module, a reagent module, and a sterilization and storage module. A floatable intake mechanism floats just below the surface of the pond to draw relatively clean water therein. The individual components of the module can be used in the absence of the other components. Various reagent modules can be added or deleted to create different intravenously injectable solutions from different water sources. If oral hydration of a patient suffering from an ion imbalance is possible (i.e., the patient is conscious), the potable water maker module 12 can be used with an appropriate reagent module 16. Therefore, the invention is not to be limited by the above disclosure, but is to be determined in scope by the claims which follow.

I claim:

1. A reagent/drug cartridge containing formulations of soluble reagents or soluble drugs for preparation of solutions and enhance the rate of dissolution of said reagents or drug with a fluid diluent, comprising:

a casing having a fluid inlet for accepting a diluent and a fluid outlet for expelling a solution, and having fluid manifolds adjacent to the inlet and outlet for directing fluid in a radial direction from the inlet to the outlet, the casing further defining a receptacle between the inlet and outlet for receiving a soluble reagent or drug;

a soluble reagent or drug in the receptacle; and, a reagent/drug compression means disposed within said casing for compression of the reagent or drug to minimize interstitial spaces between particles of said reagent or drug and enhance the rate of dissolution of the reagent or drug upon introduction of the diluent into the inlet.

2. The reagent/drug cartridge of claim 1, wherein the reagent or drug bed compression means is a resilient sponge material having a compressed volume and an expanded volume and adequate pressure upon compression to minimize interstitial spaces between particles of reagent or drug, wherein the expanded volume is up to at least 500% of the compressed volume and exceeds the internal volume of the container.

3. The reagent/drug cartridge of claim 2, wherein the resilient sponge material consists of a first sponge located adjacent to the fluid inlet, and a second sponge located adjacent to the fluid outlet.

4. The reagent/drug cartridge of claim 1, wherein the reagent/drug compression means is a resilient coiled spring having a compressed volume and an expanded volume and adequate pressure upon compression to compress the reagent or drug minimize interstitial spaces between particles, wherein the expanded volume is up to at least 500% of the compressed volume and expanded volume fills to greater than the internal volume of the container.

5. The reagent/drug cartridge of claim 4, including a fluid permeable pressure plate adjacent to a free end of the coiled spring and wherein the reagent is positioned against the pressure plate.

6. A method for obtaining injectable quality intravenous solution comprising the steps of:

selecting an appropriate reagent/drug cartridge module; quickly connecting the reagent/drug cartridge module intermediate a potable raw water intake and treatment mechanism and an intravenous bag;

passing treated potable water to said reagent/drug cartridge module; completely compressing the reagent/drug by pressure from a resilient sponge disposed in said reagent/drug cartridge module, as the reagent dissolves;

operating the potable raw water intake and treatment mechanism until the bag is full and the reagent is consumed; and removing the bag.

7. The method of claim 6, including the sequential steps of passing the raw water through a microfiltration stage, a deionizing stage, and an activated carbon bed stage before passing the treated water through the reagent/drug module.

8. A method for obtaining drug containing solution, comprising the steps of:

selecting an appropriate drug cartridge module having the drug disposed within a casing;

connecting the drug cartridge module intermediate with a diluent source and a drug containing solution administration means;

completely and continuously compressing the drug in said cartridge with a resilient sponge disposed within said casing as the drug completely dissolves as diluent passes through the drug.

* * * * *